US012727970B2

(12) United States Patent
Phan

(10) Patent No.: US 12,727,970 B2
(45) Date of Patent: Sep. 8, 2026

(54) ORTHODONTIC DEVICES FOR DELIVERY OF AN ACTIVE AGENT

(71) Applicant: Smylio Inc., Fremont, CA (US)

(72) Inventor: Loc Phan, Santa Clara, CA (US)

(73) Assignee: Smylio Inc., Fremont, CA (US)

( * ) Notice: Subject to any disclaimer, the term of this patent is extended or adjusted under 35 U.S.C. 154(b) by 96 days.

(21) Appl. No.: 18/716,133

(22) PCT Filed: Dec. 7, 2022

(86) PCT No.: PCT/US2022/081126

§ 371 (c)(1),
(2) Date: Jun. 3, 2024

(87) PCT Pub. No.: WO2023/108032

PCT Pub. Date: Jun. 15, 2023

(65) Prior Publication Data

US 2025/0032221 A1 Jan. 30, 2025

Related U.S. Application Data

(60) Provisional application No. 63/287,023, filed on Dec. 7, 2021.

(51) Int. Cl.
*A61C 7/08* (2006.01)
*A61C 19/06* (2006.01)
(Continued)

(52) U.S. Cl.
CPC .............. *A61C 7/08* (2013.01); *A61C 19/066* (2013.01); *A61K 8/21* (2013.01); *A61K 31/4045* (2013.01);
(Continued)

(58) Field of Classification Search
CPC ............................ A61C 19/066; A61C 19/063
See application file for complete search history.

(56) References Cited

U.S. PATENT DOCUMENTS 5,194,003 A * 3/1993 Garay .................. A61K 9/0063 433/229
5,326,685 A * 7/1994 Gaglio ................. A61C 19/063 433/215
(Continued)

FOREIGN PATENT DOCUMENTS

CN 113616363 A * 11/2021 ........... A61C 19/063
GB 2584471 A * 12/2020 ........... A61K 31/165
(Continued)

OTHER PUBLICATIONS

Fouquet M., International Search Report & Written Opinion for PCT/US2022/081126, May 11, 2023.

*Primary Examiner* — Heidi M Eide
(74) *Attorney, Agent, or Firm* — MT HUNT LAW; Marcus T. Hunt

(57) ABSTRACT

Devices configured for insertion into an oral cavity of a subject for delivery of an agent for a time period are described. The devices are comprised of at least two polymer shells that nest or stack to create a space or gap therebetween. The agent is placed in the gap and is released in a controlled fashion to deliver agent for the time period. Kits comprised of a device and optionally a refill of the agent are also described.

35 Claims, 3 Drawing Sheets

(51) Int. Cl.

| | |
|---|---|
| ***A61K 8/21*** | (2006.01) |
| ***A61K 31/4045*** | (2006.01) |
| ***A61K 31/405*** | (2006.01) |
| ***A61Q 11/00*** | (2006.01) |

(52) U.S. Cl.

CPC ............ *A61K 31/405* (2013.01); *A61Q 11/00* (2013.01); *A61C 2201/00* (2013.01)

(56) References Cited

U.S. PATENT DOCUMENTS

| | | | | |
|---|---|---|---|---|
| 5,842,860 | A * | 12/1998 | Funt .................... | A61M 31/002 433/80 |
| 2002/0182154 | A1 | 12/2002 | McLaughlin | |
| 2003/0211440 | A1* | 11/2003 | Kuo .................... | A61C 19/063 433/215 |
| 2009/0136893 | A1* | 5/2009 | Zegarelli .............. | A61C 19/066 433/80 |
| 2016/0157962 | A1* | 6/2016 | Kim ........................ | B29C 65/48 156/242 |
| 2016/0278899 | A1* | 9/2016 | Heller .................. | A61K 31/198 |
| 2017/0189154 | A1* | 7/2017 | Allen ...................... | B29C 51/10 |
| 2020/0237480 | A1 | 7/2020 | Phan | |
| 2021/0137641 | A1 | 5/2021 | Phan et al. | |
| 2022/0034691 | A1 | 2/2022 | Fell et al. | |
| 2022/0265393 | A1 | 8/2022 | Phan et al. | |
| 2024/0050197 | A1* | 2/2024 | Gagnon ................. | A61C 19/06 |

FOREIGN PATENT DOCUMENTS

| | | | | |
|---|---|---|---|---|
| WO | 2002024100 | A1 | 3/2002 | |
| WO | WO-2013190580 | A1 * | 12/2013 | ............... A61C 7/08 |
| WO | 2020079555 | A1 | 4/2020 | |
| WO | 2020141444 | A1 | 7/2020 | |
| WO | 2021137159 | A1 | 7/2021 | |

* cited by examiner

ORTHODONTIC DEVICES FOR DELIVERY OF AN ACTIVE AGENT

CROSS-REFERENCE TO RELATED APPLICATIONS

This application is a national stage application pursuant to 35 U.S.C. § 371 of International Application No. PCT/US2022/081126, filed Dec. 7, 2022, which claims the benefit of U.S. Provisional Application No. 63/287,023, filed Dec. 7, 2021, the entireties of which are incorporated by reference herein.

TECHNICAL FIELD

The subject matter described herein relates orthodontic devices, and more particularly, to the controlled release of an active agent from the device.

BACKGROUND

Clear aligners for orthodontic treatment have become an accepted approach due to their essentially invisible nature and ease of wear. Transparent devices as retainers, mouth guards and night guards are also widely used. These devices offer a simple way to deliver an active agent to the oral cavity, whether for therapeutic, cosmetic or non-therapeutic reasons. The present disclosure provides a device for controlled delivery of an active agent to the oral cavity.

BRIEF SUMMARY

The following aspects and embodiments thereof described and illustrated below are meant to be exemplary and illustrative, not limiting in scope.

In one aspect, a device is provided. The device is comprised of a first polymer shell contoured to fit at least a portion of a subject's upper or lower teeth, the first polymer shell having an inner surface, an outer surface, and a first shell edge member; a second polymer shell dimensioned to receive the first polymer shell, the second polymer shell having an inner receiving surface and an outer external surface, and a second shell edge member, the first edge member and the second edge member are joined to form a gap between the inner surface and the inner receiving surface; and an agent disposed in the gap. The device is configured for insertion into an oral cavity of a subject for delivery of the agent for controlled release over a time period.

In another aspect, a kit comprising a device and an active agent is provided. The device is comprised of a first polymer shell contoured to fit at least a portion of a subject's upper or lower teeth, the first polymer shell having an inner surface, an outer surface, and a first shell edge member; a second polymer shell dimensioned to receive the first polymer shell, the second polymer shell having an inner receiving surface and an outer external surface, and a second shell edge member, the first edge member and the second edge member are joined to form a gap between the inner surface and the inner receiving surface. The active agent is configured for insertion into the gap. The device is configured for insertion into an oral cavity of a subject for delivery of the active agent for a period of time.

In one embodiment, the first shell edge member is comprised of an inner edge, an outer edge, or both an inner edge and an outer edge.

In one embodiment, one or both of the inner edge and outer edge of the first shell edge forms an arch.

In one embodiment, the second shell edge member is comprised of an inner edge, an outer edge, or both an inner edge and an outer edge.

In one embodiment, one or both of the inner edge and outer edge of the second shell edge forms an arch.

In one embodiment, the inner edge and the outer edge of the second shell each form an arch with a length, respectively, of $l_{2\text{-}inner}$ and $l_{2\text{-}outer}$, and the inner edge and the outer edge of the first shell each form an arch with a length, respectively, of $l_{1\text{-}inner}$ and $l_{1\text{-}outer}$, and the first shell inner edge and the second shell inner edge are sealed along the lengths $l_{1\text{-}inner}$ and $l_{2\text{-}inner}$, and the first shell outer edge and the second shell outer edge are sealed along the lengths $l_{1\text{-}outer}$ and $l_{2\text{-}outer}$, to form a peripheral edge seal.

In one embodiment, the inner edge and the outer edge of the second shell each form an arch with a length, respectively, of $l_{2\text{-}inner}$ and $l_{2\text{-}outer}$, and the inner [lingual] edge and the outer [buccal] edge of the first shell each form an arch with a length, respectively, of $l_{1\text{-}inner}$ and $l_{1\text{-}outer}$, and the first shell inner edge and the second shell inner edge are sealed at one or more discrete points along the lengths $l_{1\text{-}inner}$ and $l_{2\text{-}inner}$, and the first shell outer edge and the second shell outer edge are sealed are sealed at one or more discrete points along the lengths $l_{1\text{-}outer}$ and $l_{2\text{-}outer}$, to form a plurality of peripheral edge sealing points.

In one embodiment, the device further comprises a third polymer shell dimensioned to receive the second polymer shell, the third polymer shell having an inner receiving surface and an outer external surface, and a third shell edge member.

In one embodiment, the third shell edge member is comprised of an inner edge, an outer edge, or both an inner edge and an outer edge.

In one embodiment, the third shell edge member is joined at one or more discrete points to the second shell edge member, and where a gap is formed between the inner receiving surface of the third shell member and the outer external surface of the second shell member.

In one embodiment, the device when inserted into an oral cavity of a subject is further configured to apply force to teeth for a wear period, for movement of teeth from an existing position to a next position.

In one embodiment, the device is a retainer, the retainer not configured to apply force to teeth to reach a final tooth position but to maintain teeth in a final tooth position, wherein the retainer is designed to be worn in the mouth for a wear period.

In one embodiment, the wear period is longer than the release period, or wherein the release period is longer than the wear period, or wherein the wear period and the release period are essentially the same.

In one embodiment, one or more of the first, second and third polymer shells is a laminate of at least two polymeric materials.

In one embodiment, the laminate is a di-laminate or a tri-laminate comprised a first thermoplastic material and a second thermoplastic material.

In one embodiment, the first thermoplastic material along has a transparent appearance.

In one embodiment, the second thermoplastic material is translucent.

In one embodiment, the second thermoplastic material is a copolyester.

In one embodiment, the laminate comprises a transparent copolyester.

In one embodiment, the transparent copolyester is polyethylene terephthalate glycol-modified (PETG).

In one embodiment, the laminate comprises a polyurethane or a maleic anhydride grafted polyethylene.

In one embodiment, the laminate is a tri-laminate comprised of a middle layer of a polyurethane disposed between first and second layers of PETG.

In one embodiment, the laminate is a tri-laminate comprised of a middle layer of a PETG disposed between first and second layers of a polyurethane.

In one embodiment, the device or kit comprises an amount of agent for release at a controlled rate for the release period or for the time period.

In one embodiment, the device or kit comprises a second agent, a third agent and/or a fourth agent.

In one embodiment, the device comprises a second gap, and the second agent is disposed in the second gap.

In one embodiment, the second agent is released from the device at a rate different from the agent.

In one embodiment, the active agent is formulated with one or more excipients to obtain a formulation, and the formulation controls release of the agent from the device.

In one embodiment, the agent is formulated with one or more excipients to obtain a formulation, and release of agent from the device is controlled by the first polymer shell or the second polymer shell.

In one embodiment, the agent is formulated with one or more excipients to obtain a formulation, and release of agent from the device is controlled by the peripheral edge seal.

In one embodiment, the agent is formulated with one or more excipients to obtain a formulation, and release of agent from the device is controlled by the peripheral edge sealing or by a plurality of peripheral edge sealing points.

In one embodiment, one or more of the polymer shells is a porous shell member.

In one embodiment, the agent is a breath freshener. In one embodiment, the agent is selected from a mint, cinnamon, and a fruit flavor.

In one embodiment, the agent is a nutritional agent or nutritional (dietary) supplement.

In one embodiment, the agent is selected from vitamins, minerals, antioxidants, and sleep agents.

In one embodiment, the agent is melatonin or 5-hydroxytryptophan or other sleep aide.

In one embodiment, the agent is an oral or dental wellness agent.

In one embodiment, the agent is stannous fluoride or sodium fluoride.

In one embodiment, the agent is a therapeutic agent with activity for tissue remodeling.

In one embodiment, the agent is released over a period of at least about 6 hours, 8 hours, 12 hours, 18 hours, 24 hours, 36 hours, 48 hours or 72 hours.

In one embodiment, a support member or carrier is positioned in the gap, wherein the support member is configured to releasably carry the agent.

In one embodiment, the support member or carrier is a foam, a population of microporous particles, or a fabric, such as a porous, woven, or non-woven fabric.

In one embodiment, the kit comprises one or more refills of the agent. In one embodiment, the kit comprises a second agent, and/or one or more refills of the second agent.

In addition to the exemplary aspects and embodiments described above, further aspects and embodiments will become apparent by reference to the drawings and by study of the following descriptions.

Additional embodiments of the present device, kit, methods and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present disclosure. Additional aspects and advantages of the present disclosure are set forth in the following description and claims, particularly when considered in conjunction with the accompanying examples and drawings.

DETAILED DESCRIPTION

I. Definitions

Figure 1A:
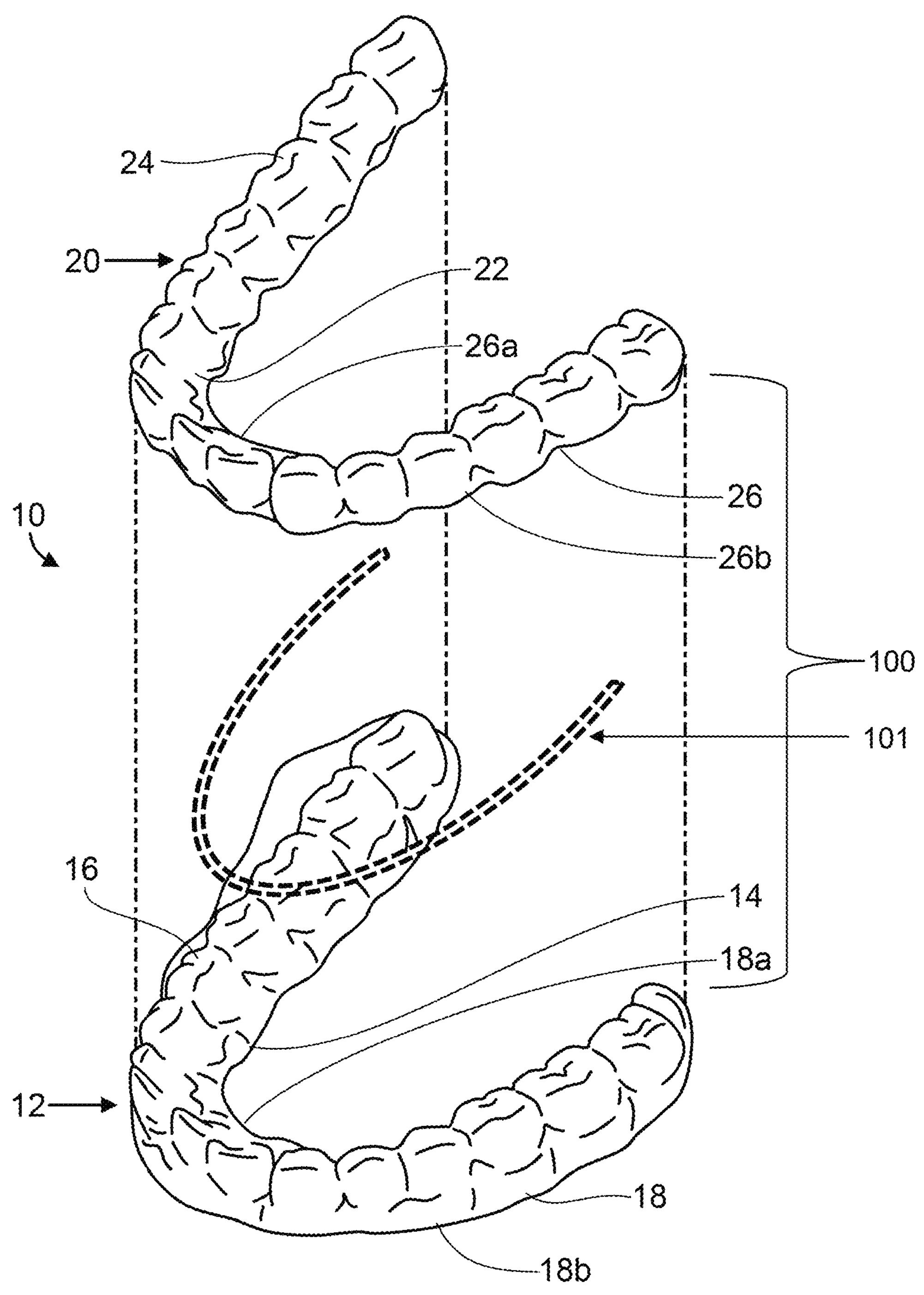
FIG. 1A is an exploded drawing of a device configured to be worn in the mouth of a human for release of an active agent.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

The compositions of the present disclosure can comprise, consist essentially of, or consist of, the components disclosed.

All percentages, parts and ratios are based upon the total weight of the topical compositions and all measurements made are at about 25° C., unless otherwise specified.

The terms "tooth" and "teeth" include natural teeth, including natural teeth which have been modified by fillings or by crowns, implanted teeth, artificial teeth that are part of a bridge or other fitting secured to one or more natural or implanted teeth, and artificial teeth that are part of a removable fitting.

By reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by reserving the right to proviso out or exclude any individual substituents, analogs, compounds, ligands, structures, or groups thereof, or any members of a claimed group, less than the full measure of this disclosure can be claimed for any reason.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

II. Devices and Kits

FIG. 1 illustrates an embodiment of a device 10 configured to be worn in the mouth of a human. Device 10, shown in exploded view, is comprised of a first polymer shell 12 that is contoured to fit at least a portion of a subject's upper or lower teeth. In the illustrated embodiment, first polymer shell 12 is configured to fit lower teeth in a human subject. It will be appreciated that a first polymer shell for fitting a portion of the lower or upper teeth, or for fitting the upper teeth is contemplated. The first polymer shell has an inner surface 14 configured to fit about or over, and to contact, the teeth. The inner surface can also be referred as a tooth-contacting surface. The first polymer shell also comprises an outer surface 16 and a first shell edge member 18. Edge member 18 is composed of an inner or lingual edge region 18*a* and an outer or labial/buccal edge region 18*b*.

Device 10 also comprises a second polymer shell 20 that is dimensioned to receive the first polymer shell 12. Second polymer shell 20 is configured to fit over all or a portion of outer surface 16 of first polymer shell 12. Second polymer shell 20 has an inner receiving surface 22, an outer external surface 24, and a second shell edge member 26. Second shell edge member 26 is composed of an inner or lingual edge region 26*a* and an outer or labial/buccal edge region 26*b*.

Figure 1B:
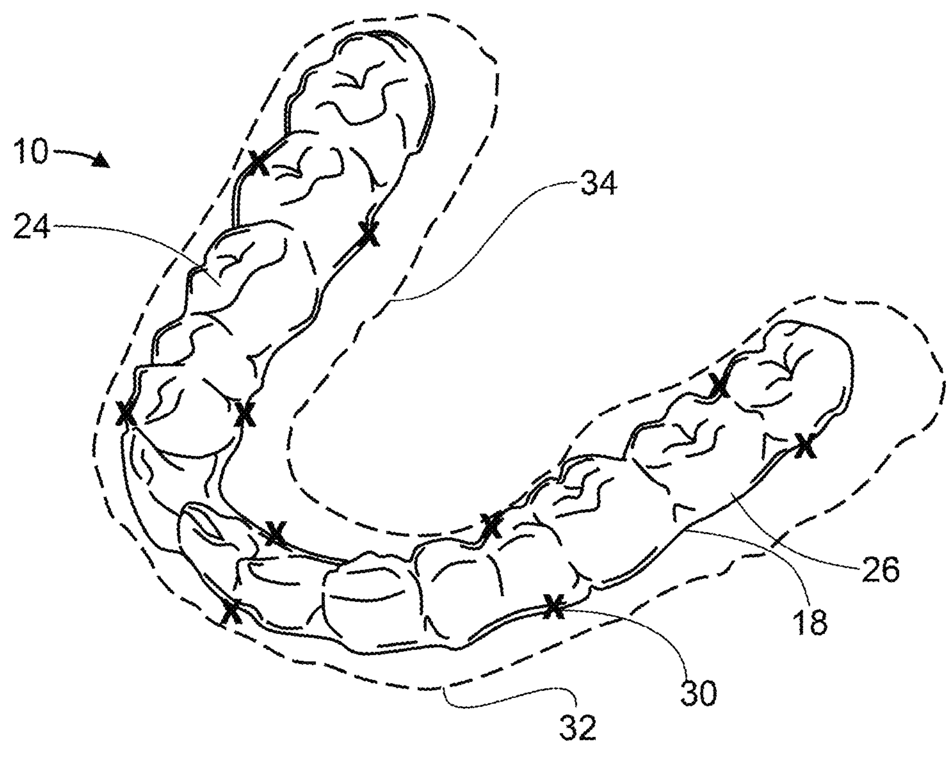
FIG. 1B shows a device where the first and second polymer shells are nested or engaged, to create a gap therebetween.

Turning now to FIG. 1B, the device 10 is shown where the first and second polymer shells are nested or engaged. That is, the first and second polymer shells can be stacked loosely, e.g., without a compressive or an interference fit between shells or such that an upturned stack of shells self-disassembles, before being made substantially affixed or varyingly affixed, as will be described. Inner receiving surface 22 of second polymer shell 20 is nested with or stacked over outer surface 16 of first polymer shell 12. First edge member 18 and second edge member 26 are joined, at least partially, as will be described. A gap (represented by reference numeral 100 in FIG. 1A), not visible in FIG. 1B, is created when the first and second polymer shells are nested together, the gap having as a "ceiling" or upper boundary the inner receiving surface 22 of the second polymer shell and as a "floor" or lower boundary the outer surface 16 of the first polymer shell. As will be described infra an agent (represented by reference numeral 101 in FIG. 1A) is placed in the gap for delivery over a time period to a subject wearing the device. In one embodiment, the reference numeral 101 shown in FIG. 1A may represent a support member or carrier that is positioned in the gap and configured to releasably carry the agent. In one embodiment, the support member or carrier is a foam, a population of microporous particles, or a fabric, such as a porous, woven, or non-woven fabric.

The first and second polymer shells can be joined at discrete points along the first edge member and the second edge member, such as the discrete points indicated in FIG. 1B by the X symbols, where X symbol 30 is representative. In this embodiment, agent disposed in the gap may be formulated into a controlled release formulation that controls its delivery from the device. In another embodiment, the first and second polymer shells It will be appreciated that the device depicted in FIGS. 1A-1B can be modified to fit over a portion of the teeth in the upper and/or lower jaw rather than all the teeth as depicted. For example, the device can be configured to fit the teeth on the lower right side of the mouth, or the upper left side of the mouth. Or the device can be configured to fit over one, two, three, or four molars on one or both sides of the mouth.

In an embodiment, one or both of the inner edge and outer edge of the first shell edge forms an arch. This is illustrated in FIG. 1B, where the dashed line 32 forms an arch that runs along the outer edge member 18*b* of the first shell member. Dashed line 34 forms an arch that runs along the inner edge member18*a*. In this embodiment where the device is configured to cover all the teeth of the lower jaw, arch 32 and arch 34 are joined at the back molars.

In one embodiment, the inner edge and the outer edge of the second shell each form an arch with a length, respectively, of $l_{2\text{-}inner}$ and $l_{2\text{-}outer}$, and the inner edge and the outer edge of the first shell each form an arch with a length, respectively, of $l_{1\text{-}inner}$ and $l_{1\text{-}outer}$, and the first shell inner edge and the second shell inner edge are sealed along the lengths $l_{1\text{-}inner}$ and $l_{2\text{-}inner}$, and the first shell outer edge and the second shell outer edge are sealed along the lengths $l_{1\text{-}outer}$ and $l_{2\text{-}outer}$, to form a peripheral edge seal.

In one embodiment, the inner edge and the outer edge of the second shell each form an arch with a length, respectively, of $l_{2\text{-}inner}$ and $l_{2\text{-}outer}$, and the inner edge and the outer edge of the first shell each form an arch with a length, respectively, of $l_{1\text{-}inner}$ and $l_{1\text{-}outer}$, and the first shell inner edge and the second shell inner edge are sealed at one or more discrete points along the lengths $l_{1\text{-}inner}$ and $l_{2\text{-}inner}$, and the first shell outer edge and the second shell outer edge are sealed are sealed at one or more discrete points along the lengths $l_{1\text{-}outer}$ and $l_{2\text{-}outer}$, to form a plurality of peripheral edge sealing points.

As mentioned above, the agent can be formulated with one or more excipients to obtain a formulation, and the formulation controls release of the agent from the device. This embodiment is desired when the first shell outer edge and the second shell outer edge are sealed are sealed at one or more discrete points along the lengths $l_{1\text{-}outer}$ and $l_{2\text{-}outer}$, to form a plurality of peripheral edge sealing points. In embodiments where the first shell inner edge and the second shell inner edge are sealed along the lengths $l_{1\text{-}inner}$ and $l_{2\text{-}inner}$, and the first shell outer edge and the second shell outer edge are sealed along the lengths $l_{1\text{-}outer}$ and $l_{2\text{-}outer}$, to form a peripheral edge seal, the agent may or may not be formulated with one or more excipients to obtain a formulation, as release of agent from the device is controlled by the first polymer shell and/or the second polymer shell. Of course, release of the agent can also be dependent upon or controlled by the peripheral edge seal by making the seal more permeable to the agent than the material from which the polymer shells are fabricated. In one embodiment, the peripheral edge seal extends along the entire length of the nested polymer shells, so that the gap between the polymer shells is substantially entirely sealed from the external environment. During use, saliva from the mouth is unable to migrate into the gap. In embodiments, the peripheral edge seal is semi-permeable to the agent. In other embodiments, the peripheral edge seal is hermetic.

In one embodiment, the agent is formulated with one or more excipients to obtain a formulation, and release of agent from the device is controlled by the peripheral edge sealing or by a plurality of peripheral edge sealing points.

Figure 2:
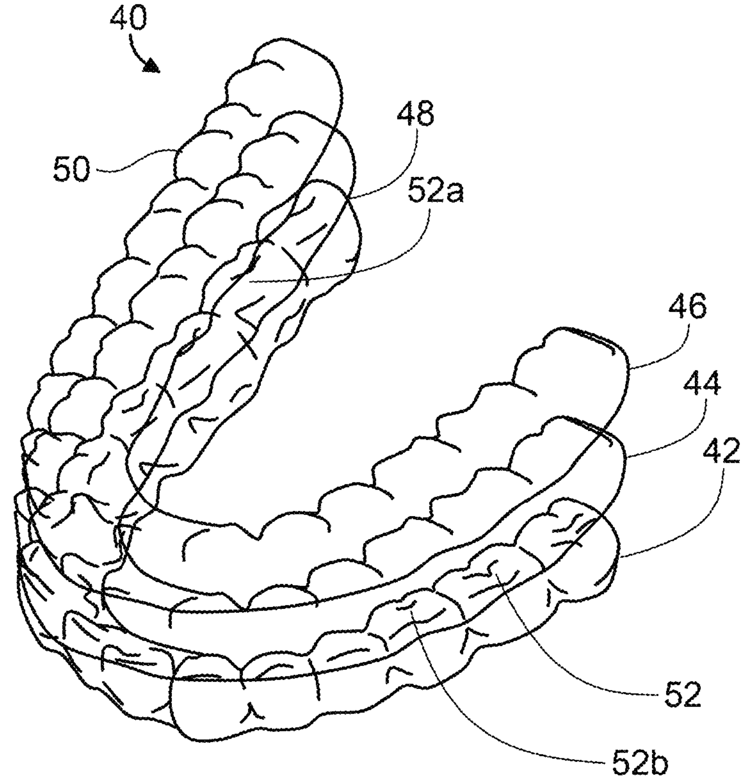
FIG. 2 illustrates a device comprised of first, second and third polymer shells, with gaps between the first and second polymer shells and between the second and third polymer shells, where each gap can receive or contains an agent.

Optionally, one or more additional shells can be located between the first polymer shell and the second polymer shell. This embodiment is shown in FIG. 2, where a device comprising a third polymer shell is depicted. Device 40 is comprised of a first polymer shell 42, a second polymer shell 44, and a third polymer shell 46. Third polymer shell 46 has an inner receiving surface 48 and an outer external surface 50, and a third shell edge member 52. The third shell edge member is comprised of an inner edge 52*a*, an outer edge 52*b*, or both an inner edge and an outer edge.

The third shell edge member is joined at one or more discrete points to the second shell edge member. A gap is formed between the inner receiving surface of the third shell member and the outer external surface of the second shell member. An agent is placed or configured to be placed in the gap, where the agent can be the same agent or a different agent from the agent placed in the gap created between the first polymer shell and the second polymer shell.

Figure 3:
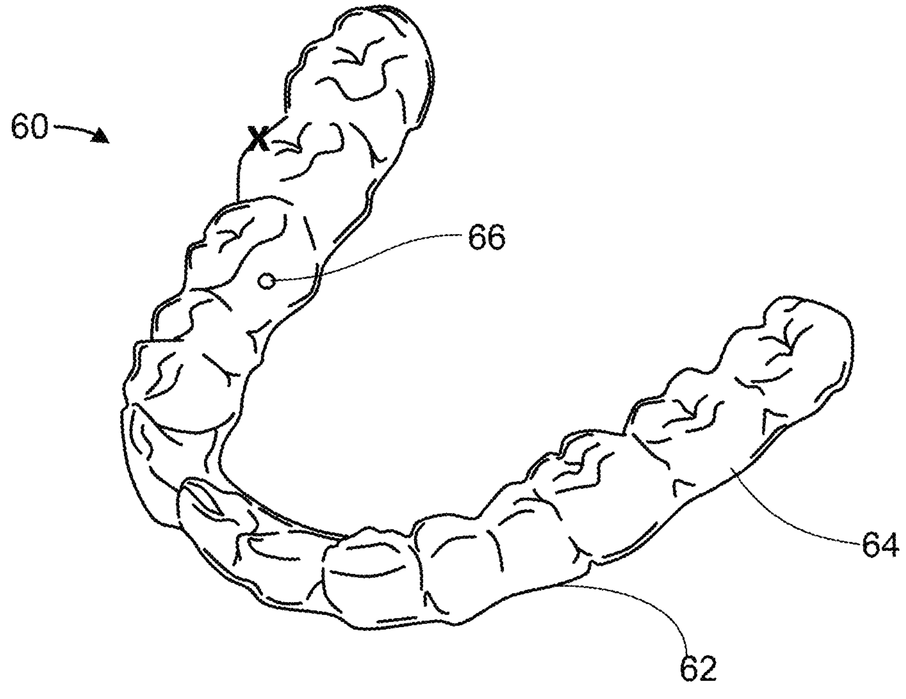
FIG. 3 illustrates a device with first and second nested polymer shells to create a gap therebetween and with one or more openings for release of an agent placed in the gap.

In an embodiment, one or more of the polymer shells has one or more openings or ports for release of an agent disposed in the gap between adjacent or nested polymer shells. With reference to FIG. 3, device 60 is comprised of a first polymer shell 62 and a second polymer shell 64. It will be appreciated that device 60 can have additional polymer shells. In this embodiment, one or more of the polymer shells has an opening, such as opening 66 in polymer shell 64. The opening can be created, for example, by placing or inserting a wire of any applicable gauge into the polymer during molding of the polymer shell or by drilling the opening into the polymer shell after it is manufactured. A device can have 1, 2, 3, 4, 5, 6, 7, 8, 9, 10 or more openings. The opening creates an pathway for release of agent placed in the gap, where control of the release can be influenced by the size of the opening and/or the formulation in which the agent resides.

In an embodiment of any of the devices described herein, a device configured for placement on the maxilla comprises a first agent, and a device configured for placement on the mandible of the same subject comprises a different second agent. In an embodiment, the first agent and the second agent have complementary functions or have independent functions.

The devices described herein can be configured to apply force to teeth for a wear period, for movement of teeth from an existing position to a next position. Alternatively, the device is not designed or configured to apply force to cause movement of one or more teeth, but is configured for insertion and release on or over one or more teeth as a retainer or mouth guard. The device is configured to hold teeth in an existing position. The device can function as a retainer that is used post orthodontic treatment where teeth were moved, or the device can function for the purpose of delivery of the active agent to the oral cavity. In other embodiments, the device is an orthodontic, prosthetic, retaining, snoring/airway, cosmetic, therapeutic, protective (e.g., mouth guards) or habit-modification device.

The devices, whether for tooth movement or not, are intended to be worn for a wear period. In one embodiment, the wear period is longer than the time period during which agent is released from the device. In another embodiment, the time period during which agent is released from the device is longer than the wear period. In another embodiment, the wear period and time period during which agent is released from the device are essentially the same.

For example, the wear period can be 24 hours, and the time period for release of agent can be 24 hours or less. If less, the user can be provided with additional agent to place in the gap or gaps of the device. In another example, the wear period can be 18 hours, and the time period for release can be 6 hours. The user can refill the device when release diminishes with the same or a different agent. In another example, the wear period is 6-10 hours, and the time period for release is 4-8 hours, so that agent is provided for more than 50% of the wear period.

It will also be appreciated that a device comprising a first agent in a first gap and a second agent in a second gap can be configures so that the first agent and the second agent release at different rates or for different time periods. For devices with more than three polymer shells, and thus more than two gaps, third, fourth and more agents can be placed in the device, where the agents can be the same, different, released at the same or different rates, and/or released for the same or different time periods.

Release of the agent (also referred to herein as an active agent) to the oral cavity includes release to the soft tissues of the mouth. The soft tissue of the inside of the mouth, includes but is not limited to any soft tissue adjacent or between the teeth, including but not limited to the papilla, tissue of the upper and lower dental arches, marginal gingiva, gingival sulcus, inter-dental gingiva, gingival gum structure on lingual and buccal surfaces up to and including the muco-gingival junction and/or the upper palate and/or the floor of the mouth. The soft tissue area includes the muco-buccal folds, hard and soft palates, lining mucosa, the tongue and/or attached gingival tissue. In some embodiments, the device or oral appliance receives one or more teeth including one or more molars, premolars, incisors, cuspids, tooth implant, or combination or portions thereof. In other embodiments, the active agent contained in the oral appliance can be disposed anywhere within the gap formed between two shells of the device, as described above, for release in specific areas of the mouth cavity. For example, the active agent can be positioned in the gap between two shells where the shell that fits about the teeth (e.g., the first polymer shell) contacts specific teeth, such as the molars or the incisors, for release of the agent near the molars or near the incisors, as the case may be.

Materials for the Polymer Shells

The first, second, third or more polymer shells of the device can be manufactured of the same or different materials. Exemplary materials for forming the shells is now described.

In a first embodiment, one or more of the first, second, third or more polymer shells is each individually a laminate of at least two polymeric materials. The laminate can be a di-laminate or a tri-laminate comprised of a first thermoplastic material, a second thermoplastic material, and optionally a third thermoplastic material. In one embodiment, the first thermoplastic material along has a transparent appearance and/or the second thermoplastic material is translucent. By way of example, the second thermoplastic material can be a copolyester. The first thermoplastic material can be a transparent copolyester, and an exemplary material is polyethylene terephthalate glycol-modified (PETG).

In a second embodiment, one or more of the first, second, third or more polymer shells is each individually a tri-laminate comprised of a polyurethane or a maleic anhydride grafted polyethylene. For example, a shell or at least one of the polymer shells in the device can be a polymer laminate with three layers, A, B and C, where layers A and C are outer layer with layer B in the middle positioned between layers A and C. In an embodiment, the A and C layers individually comprise a thermoplastic polymer having a modulus of from about 1,000 MPa to 2,500 MPa and a glass transition temperature and/or melting point of from about 80° C. to 180° C. and the middle B layer is comprised of at least an elastomer having a modulus of from about 50 MPa to about 500 MPa and one or more of a glass transition temperature and/or melting point of from about 90° C. to about 220° C.

In one embodiment, the A and C layers are comprised of one of more of a co-polyester, a polycarbonate, a polyester polycarbonate blend, a polyurethane, a polyamide or a polyolefin. In another embodiment, the middle B layer is comprised of one or more of a polyurethane elastomer, a polyolefin elastomer, a polyester elastomer, a styrenic elastomer, a polyamide elastomer, a cyclic olefin elastomer, an acrylic elastomer, an aromatic or aliphatic polyether and a polyester polyurethane.

In another embodiment, one or more of the A and C layers comprises a co-polyester comprised of: (a) a dicarboxylic acid component comprising 70 mole % to 100 mole % of terephthalic acid residues, and (b) a diol component comprising i) 0 to 95% ethylene glycol, ii) 5 mole % to 50 mole % of 2,2,4,4-tetramethyl-1,3-cyclobutanediol residues, and iii) 50 mole % to 95 mole % 1,4-cyclohexanedimethanol residues, iiii) 0 to 1% of a polyol having three or more hydroxyl groups, wherein the sum of the mole % of diol residues i) and ii) and iii) and iiii) amounts to 100 mole % and the copolyester exhibits a glass transition temperature Tg from 80° C. to 150° C. In another embodiment, the middle B layer comprises an aromatic polyether polyurethane having a Shore hardness of from about A90 to D55, from about A85 to D60, or from about A80 to D65, and a compression set of less than 35%, wherein the interlayer peel strength between the A and C layers and the B layer is greater than 50 N per 2.5 cm. "Compression set" refers to a permanent deformation of a material when a force is applied and removed, and can be measured according to ASTM D 305-B at specified time and temperature, for example 22 hours at 23° C.

In one embodiment, one or more of the A and C layers comprises a polyurethane comprised of (a) a di-isocyanate comprising 80 mole % to 100 mole % of methylene diphenyl diisocyanate residues and/or hydrogenated methylene diphenyl diisocyanate and (b) a diol component comprising i) 0 to 100 mole % hexamethylene diol and ii) 0 to 50 mole % 1,4-cyclohexanedimethanol, wherein the sum i) and ii) amounts to greater than 90 mole % and the polyurethane has a glass transition temperature Tg from about 85° C. to about 150° C. Other laminates for an individual polymer shell in the devices described herein are described in U.S. Pat. Nos. 10,870,263, 10,549,511; and 10,987,907, which are incorporated by reference herein.

In one embodiment, the laminate is a tri-laminate comprised of a middle layer of a polyurethane disposed between first and second layers of PETG. In another embodiment, the laminate is a tri-laminate comprised of a middle layer of a PETG disposed between first and second layers of a polyurethane.

More generally, each shell can be constructed entirely from a single layer of or from two or more layers of a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate or a combination thereof.

In some embodiments, shells are coated with lubricous materials or provided with surface treatments. In some embodiments, interior portions of the shells are treated with hydrophobic coatings. In some embodiments, shells of relatively more flexibility can be used in conjunction with stiffer shells. Flexible shells can be constructed from hydrogels, styrenic block copolymers (SBC), silicone rubbers, elastomeric alloys, thermoplastic elastomers (TPE), thermoplastic vulcanizate (TPV) elastomers, polyurethane elastomers, block copolymer elastomers, polyolefin blend elastomers, thermoplastic co-polyester elastomers, thermoplastic polyamide elastomers, or a combination thereof. Flexible shells may also provide the benefit of a gasket to prevent liquid intrusion between the shells.

The shell individually can have thicknesses ranging from between about 0.025-0.80 mm, 0.025-0.70 mm, 0.025-0.60 mm, 0.025-0.55 mm, 0.025-0.50 mm, 0.025-0.40 mm, 0.025-0.30 mm, 0.025-0.20 mm, 0.025-0.15 mm, 0.025-0.10 mm, 0.025-0.09 mm, 0.025-0.08 mm, 0.025-0.07 mm, 0.025-0.06 mm, 0.025-0.05 mm, 0.025-0.04 mm, 0.05-0.80 mm, 0.05-0.70 mm, 0.05-0.60 mm, 0.05-0.55 mm, 0.05-0.50 mm, 0.05-0.40 mm, 0.05-0.30 mm, 0.05-0.20 mm, 0.05-0.15 mm, 0.05-0.10 mm, 0.05-0.09 mm, 0.05-0.08 mm, 0.05-0.07 mm, 0.05-0.06 mm, 0.075-0.80 mm, 0.075-0.70 mm, 0.075-0.60 mm, 0.075-0.55 mm, 0.075-0.50 mm, 0.075-0.40 mm, 0.075-0.30 mm, 0.075-0.20 mm, 0.075-0.15 mm, 0.075-0.10 mm, or 0.075-0.09 mm.

Processes for manufacture of the devices described herein are known to skilled artisans, and are described, for example, in U.S. Patent Application Publication No. 2020/0237480, incorporated by reference herein.

Active Agents

The device is designed to delivery to a subject an agent for a period of time, as described above. The device is capable of delivery of a wide variety of agents, and exemplary agents are set forth below.

The agent can be, but is not limited to, anti-inflammatory agents, anti-infective agents (e.g., antiviral, antibacterial, antifungal agents, etc.), tissue and bone growth factors, pain management medication (e.g., analgesics, anesthetics, etc.) antineoplastic agents, tooth whitening agents, breath fresheners, anticalculus agents, antineoplastic agents, oral dermatologics, anticaries agents, nutrients, vitamins, minerals, herbal products, or mixtures thereof.

As mentioned, the device may contain more than one agent. A device that delivers a single agent is also contemplated, as are devices that can be refilled with the same or different agents. For example, a kit with a device and refills of the same or different agents can be provided to a subject. In this way, a customized treatment regimen can be provided to the subject. This provides for agent and dose adjustment capability. The amount of agent contained within the gap of a device will vary widely depending on the agent, the effective dosage required or desired, and rate of release from the device. The rate of release can be controlled by one or move of the device and the formulation in with the agent is mixed, if any. The dosage administered to the patient can be single or multiple doses and will vary depending upon a variety of factors, including the agent's pharmacokinetic properties, patient conditions and characteristics (sex, age, body weight, health, size, etc.), extent of symptoms, concurrent treatments, frequency of treatment and the effect desired.

Anti-inflammatory agents that reduce inflammation are contemplated, and can be used for subjects suffering from pain and inflammation. Suitable anti-inflammatory agents include steroidal and/or non-steroidal anti-inflammatoires. Exemplary anti-inflammatory agents include by way of example and not limitation, alclofenac; alclometasone dipropionate; algestone acetonide; alendronate sodium; alpha amylase; amcinafal; amcinafide; amcinonide; amfenac sodium; amiprilose hydrochloride; anakinra; anirolac; anitrazafen; apazone; balsalazide disodium; beclomethasone diproprionate; bendazac; benoxaprofen; benzydamine hydrochloride; betamethasone; bromelains; broperamole; budesonide; carprofen; cicloprofen; cintazone; cliprofen; clobetasol propionate; clobetasone butyrate; clopirac; cloticasone propionate; cormethasone acetate; cortisone acetate; cortodoxone; deflazacort; desonide; desoximetasone; dexamethasone dipropionate; diclofenac potassium; diclofenac sodium; diflorasone diacetate; diflumidone sodium; diflunisal; difluprednate; diftalone; dimethyl sulfoxide; drocinonide; endrysone; enlimomab; enolicam sodium; epirizole; etodolac; etofenamate; felbinac; fenamole; fenbufen; fenclofenac; fenclorac; fendosal; fenpipalone; fentiazac; flazalone; fluazacort; fludrocortisone; flufenamic acid; flumizole; flunisolide acetate; flunixin; flunixin meglumine; fluocinonide; fluocinolone acetonide; fluocortin butyl; fluorometholone acetate; fluquazone; flurandrenolide; flurbiprofen; fluretofen; fluticasone propionate; furaprofen; furobufen; halcinonide; halobetasol propionate; halopredone acetate; hydrocortisone; ibufenac; ibuprofen; ibuprofen aluminum; ibuprofen piconol; ilonidap; indomethacin; indomethacin sodium; indoprofen; indoxole; intrazole; isoflupredone acetate; isoxepac; isoxicam; ketoprofen; lofemizole hydrochloride; lomoxicam; loteprednol etabonate; meclofenamate sodium; meclofenamic acid; meclorisone dibutyrate; medrysone; mefenamic acid; mesalamine; meseclazone; methylprednisolone suleptanate; momiflumate; nabumetone; naproxen; naproxen sodium; naproxol; nimazone; nilutamide; olsalazine sodium; orgotein; orpanoxin; oxaprozin; oxyphenbutazone; pamidronate disodium; paramethasone; paranyline hydrochloride; pentosan polysulfate sodium; phenbutazone sodium glycerate; pirfenidone; piroxicam; piroxicam cinnamate; piroxicam olamine; pirprofen; prednazate; prednisolone; prifelone; prodolic acid; proquazone; proxazole; proxazole citrate; rimexolone; romazarit; salcolex; salnacedin; salsalate; sanguinarium chloride; seclazone; sermetacin; sudoxicam; sulindac; suprofen; talmetacin; talniflumate; talosalate; tebufelone; tenidap; tenidap sodium; tenoxicam; tesicam; tesimide; tetrydamine; tiopinac; tixocortol pivalate; tolmetin; tolmetin sodium; triamcinelone; triclonide; triflumidate; zidometacin; zomepirac sodium or combinations thereof.

Other anti-inflammatory agents include steroidal agents or glucocorticosteroids. Suitable glucocorticosteroids include, but are not limited to, alclometasone diproprionate, alendronate sodium, amcinonide, beclomethasone diproprionate, betamethasone, budesonide, clobetasol propionate, cortisone, dexamethasone, diflorasone diacetate, hydrocortisone, fludrocortisone; flunisolide acetate, fluocinolone acetonide, fluocinonide, fluorometholone acetate, flurandrenolide, halcinonide, medrysone; methylprednisone suleptanate, pamidronate, paramethasone, prednisolone, nilutamide, triamcinelone, or combinations thereof.

Anti-infective agents to treat infection include by way of example and not limitation, antibacterial agents; quinolones and in particular fluoroquinolones (e.g., norfloxacin, ciprofloxacin, lomefloxacin, ofloxacin, etc.), aminoglycosides (e.g., gentamicin, tobramycin, etc.), glycopeptides (e.g., vancomycin, etc.), lincosamides (e.g., clindamycin), cephalosporins (e.g., first, second, third generation) and related beta-lactams, macrolides (e.g., azithromycin, erythromycin, etc.), nitroimidazoles (e.g., metronidazole), penicillins, polymyxins, tetracyclines, or combinations thereof.

Other exemplary antibacterial agents include, by way of illustration and not limitation, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin;

clinafloxacin hydrochloride; clindamycin; clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

Exemplary analgesics include, but are not limited to, acetaminophen; alfentanil hydrochloride; aminobenzoate potassium; aminobenzoate sodium; anidoxime; anileridine; anileridine hydrochloride; anilopam hydrochloride; anirolac; antipyrine; aspirin; benoxaprofen; benzydamine hydrochloride; bicifadine hydrochloride; brifentanil hydrochloride; bromadoline maleate; bromfenac sodium; buprenorphine hydrochloride; butacetin; butixirate; butorphanol; butorphanol tartrate; carbamazepine; carbaspirin calcium; carbiphene hydrochloride; carfentanil citrate; ciprefadol succinate; ciramadol; ciramadol hydrochloride; clonixeril; clonixin; codeine; codeine phosphate; codeine sulfate; conorphone hydrochloride; cyclazocine; dexoxadrol hydrochloride; dexpemedolac; dezocine; diflunisal; dihydrocodeine bitartrate; dimefadane; dipyrone; doxpicomine hydrochloride; drinidene; enadoline hydrochloride; epirizole; ergotamine tartrate; ethoxazene hydrochloride; etofenamate; eugenol; fenoprofen; fenoprofen calcium; fentanyl citrate; floctafenine; flufenisal; flunixin; flunixin meglumine; flupirtine maleate; fluproquazone; fluradoline hydrochloride; flurbiprofen; hydromorphone hydrochloride; ibufenac; indoprofen; ketazocine; ketorfanol; ketorolac and ketorolac tromethamine; letimide hydrochloride; levomethadyl acetate; levomethadyl acetate hydrochloride; levonantradol hydrochloride; levorphanol tartrate; lofemizole hydrochloride; lofentanil oxalate; lorcinadol; lomoxicam; magnesium salicylate; mefenamic acid; menabitan hydrochloride; meperidine hydrochloride; meptazinol hydrochloride; methadone hydrochloride; methadyl acetate; methopholine; methotrimeprazine; metkephamid acetate; mimbane hydrochloride; mirfentanil hydrochloride; molinazone; morphine sulfate; moxazocine; nabitan hydrochloride; nalbuphine hydrochloride; nalmexone hydrochloride; namoxyrate; nantradol hydrochloride; naproxen; naproxen sodium; naproxol; nefopam hydrochloride; nexeridine hydrochloride; noracymethadol hydrochloride; ocfentanil hydrochloride; octazamide; olvanil; oxetorone fumarate; oxycodone; oxycodone hydrochloride; oxycodone terephthalate; oxymorphone hydrochloride; pemedolac; pentamorphone; pentazocine; pentazocine hydrochloride; pentazocine lactate; phenazopyridine hydrochloride; phenyramidol hydrochloride; picenadol hydrochloride; pinadoline; pirfenidone; piroxicam olamine; prayadoline maleate; prodilidine hydrochloride; profadol hydrochloride; propirarn fumarate; propoxyphene hydrochloride; propoxyphene napsylate; proxazole; proxazole citrate; proxorphan tartrate; pyrroliphene hydrochloride; remifentanil hydrochloride; salcolex; salethamide maleate; salicylamide; salicylate meglumine; salsalate; sodium salicylate; spiradoline mesylate; sufentanil; sufentanil citrate; talmetacin; talniflumate; talosalate; tazadolene succinate; tebufelone; tetrydamine; tifurac sodium; tilidine hydrochloride; tiopinac; tonazocine mesylate; tramadol hydrochloride; trefentanil hydrochloride; trolamine; veradoline hydrochloride; verilopam hydrochloride; volazocine; xorphanol mesylate; xylazine hydrochloride; zenazocine mesylate; zomepirac sodium; zucapsaicin or combinations thereof.

Exemplary anesthetics include by way of example and not limitation, aliflurane; benoxinate hydrochloride; benzocaine; biphenamine hydrochloride; bupivacaine hydrochloride; butamben; butamben picrate; chloroprocaine hydrochloride; cocaine; cocaine hydrochloride; cyclopropane; desflurane; dexivacaine; diamocaine cyclamate; dibucaine; dibucaine hydrochloride; dyclonine hydrochloride; enflurane; ether; ethyl chloride; etidocaine; etoxadrol hydrochloride; euprocin hydrochloride; fluroxene; halothane; isobutamben; isoflurane; ketamine hydrochloride; levoxadrol hydrochloride; lidocaine; lidocaine hydrochloride; mepivacaine hydrochloride; methohexital sodium; methoxyflurane; midazolam hydrochloride; midazolam maleate; minaxolone; nitrous oxide; norflurane; octodrine; oxethazaine; phencyclidine hydrochloride; pramoxine hydrochloride; prilocaine hydrochloride; procaine hydrochloride; propanidid; proparacaine hydrochloride; propofol; propoxycaine hydrochloride; pyrrocaine; risocaine; rodocaine; roflurane; salicyl alcohol; sevoflurane; teflurane; tetracaine; tetracaine hydrochloride; thiamylal; thiamylal sodium; thiopental sodium; tiletamine hydrochloride; zolamine hydrochloride; or combinations thereof.

Exemplary antineoplastic agents include by way of example and not limitation, acivicin; aclarubicin; acodazole hydrochloride; acrqnine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; ethiodized oil; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; gold Au 198; hydroxyurea; idarubicin hydrochloride; ifosfamide; ilmofosine; interferon alpha-2a; interferon alpha-2b; interferon. alpha n1; interferon alpha n3; interferon beta Ia; interferon gamma Ib; iproplatin; irinotecan hydrochloride; lanreotide acetate; letrozole; leucovorin in combination with fluorouracil or methotrexate; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safmgol; safingol hydrochloride; semustine; simtrazene; sparfosate sodium; sparsomycin; spirogermanium hydrochloride; spiromustine; spiroplatin; streptonigrin; streptozocin; strontium chloride Sr 89; sulofenur; talisomycin; taxane; taxoid; tecogalan sodium; tegafur; teloxantrone hydrochloride; temoporfin; teniposide; teroxirone; testolactone; thiamiprine; thioguanine; thiotepa; tiazofurin; tirapazamine; topotecan hydrochloride; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; or combinations thereof.

Oral care agents include, but are not limited to, agents for whitening, stain bleaching, stain removal, plaque removal, tartar removal, cavity prevention and treatment, tooth recalcification, oral infections, inflamed and/or bleeding gums, mucosal wounds, lesions, ulcers, aphthous ulcers, cold sores, tooth abscesses, gingivitis, periodontal disease, xerostomia, post-surgical dressings and the elimination of mouth malodor. Agents with a flavor or breath freshening effect include essential oil such as menthol, vanillin or orange oil, lemon oil, clove oil, peppermint oil, spearmint oil.

In one embodiment, the active agent is effective to treat or ameliorate xerostomia (dry mouth). Xerostomia may also be caused by salivary gland disease, various medications and other causes.

The active agent can be an anticaries agent such as xylitol, a fluoride ion source, and mixtures thereof. Examples of fluoride ion sources include, but are not limited to, sodium fluoride, stannous fluoride, indium fluoride, organic fluorides such as amine fluorides, and sodium monofluorophosphate or combination thereof.

In other embodiments, the agent is a nutrient. That is, the agent provides nutritional value to the subject. Nutrients include minerals, vitamins, oral nutritional supplements, enteral nutritional supplements, and mixtures thereof. Minerals include, but are not limited to, calcium, phosphorus, fluoride, zinc, manganese, potassium and mixtures thereof. Vitamins can be included with minerals or used separately. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Other nutrients includes nutritional supplements, such as amino acids, lipotropics, fish oil, and mixtures thereof. Amino acids include, but, are not limited to L-Tryptophan, L-Lysine, Methionine, Threonine, Levocarnitine or L-carnitine and mixtures thereof. Lipotropics include, but, are not limited to choline, inositol, betaine, linoleic acid, linolenic acid, and mixtures thereof. Fish oil contains large amounts of Omega-3 (N-3) polyunsaturated fatty acids, eicosapentaenoic acid and docosahexaenoic acid. Antioxidants may be included such as, for example, Vitamin E, ascorbic acid, Uric acid, carotenoids, Vitamin A, flavonoids and polyphenols, herbal antioxidants, melatonin, aminoindoles, lipoic acids and mixtures thereof.

Anti-pain or desensitizing agents can also be used as the agent. Such agents may include, but are not limited to, strontium chloride, potassium nitrate, natural herbs such as gall nut, Asarum, Cubebin, Galanga, scutellaria, Liangmianzhen, Baizhi, etc.

The active agent can also be an herbal product that occur in nature or come from plants. Some herbal medicaments include, but are not limited to, chondroitin sulfate, echinacea, ephedra (also called ma huang), garlic, Ginkgo biloba, ginseng, glucosamine, kava, melatonin, phytoestrogens (such as black cohosh, dong quai and soy), saw palmetto, bee pollen, St. John's wort, or a combination thereof.

In one embodiment, the active agent is not an agent for tooth whitening. In one embodiment, the active agent is not hydrogen peroxide. In one embodiment, the active agent is not a colorant.

The active agent can be formulated for convenient insertion into the gap between the polymer shells. For example, formulations of the active agent with one or more of bulking agents, disintegrants, binders and lubricants, and excipients, which have no decisive effect on the delivery of active substances, is contemplated. Examples are, alginate, bentonite (alumina silica hydrate), silica, cellulose (normally microcrystalline cellulose) or cellulose derivatives, for example methylcellulose, sodium carboxymethylcellulose, sugars such as lactose, starches, for example maize starch or derivatives thereof, for example sodium carboxymethylstarch, starch paste, phosphoric acid salts, for example di- or tricalcium phosphate, gelatin, stearic acid or suitable salts thereof, for example magnesium stearate or calcium stearate, talc, colloidal silica and similar ancillary substances.

In an embodiment, the active agent is in powder, liquid, solid, solution, or suspension (e.g., gel) form. In solution or suspension layering, the medicament and any inactive ingredients (excipients, binders, etc.) are suspended or dissolved in water or an organic solvent. The resulting liquid can be sprayed into the gap between the polymer shells, during assembly of the device. It is also contemplated to place the active agent in the form of a dry powder into the gap between the polymer shells. The drug powder may include excipients such as a binder, flow aid, inert filler, or the like.

In various embodiments, the active agent may be encapsulated in a lipid bilayer and then impregnated, coated or layered on or into the gap between the polymer shells. In other embodiments, the active agent can be encapsulated into particles or carrier on porous particles, which are then placed into the gap between the polymer shells.

In other embodiments, the active agent is formulated into a hydrogel or bioadhesive composition which is then deposited in the gap between the polymer shells. Suitable materials for hydrogels and bioadhesives include Polycarbophil, Carbopol/carbomer, Sodium carboxymethyl cellulose, hydroxypropylcellulose, hydroxypropylmethyl cellulose, hydroxyethyl cellulose, xanthan gum, guar gum, hydroxypropyl guar, carrageenan, sodium alginate, poly(hydoxy butyrate), poly(e-caprolactone and copolymers, poly(ortho esters), poly(cyano acrylates), polyphosphazenes, poly(vinyl alcohol), poly(ethylene oxide), poly(hydroxytheyl methacrylate), and poly(ethylene oxide-beta propylene oxide).

Methods of Use

A method of delivering an active agent to the oral cavity is also contemplated, where a device as described herein is placed or instructed to be placed in the mouth. The active agent is released from the device for a period of time. The agent is released to, for example, at least a portion of teeth and/or soft tissue areas inside a mouth. The agent is released for a period of, for example, at least about 2 hours, 4 hours, 6 hours, 8 hours, 12 hours, 15 hours, 18 hours, 20 hours, 24 hours, 30 hours, 36 hours, 48 hours, 72 hours.

The device can be used for delivery of active agents for pleasure, for cosmetic, or therapeutic reasons. For example, the active agent can be an essential oil, such a peppermint oil or spearmint oil, for the pleasurable sensation of the oil in the mouth and/or for freshening the breath. The active agent can be nicotine. The active agent can be a pharmaceutical for treating a disease or condition or to alleviate signs or symptoms of the disease. Alleviation can occur prior to signs or symptoms of the disease appearing, as well as after their appearance.

As can be appreciated, the device provides for localized delivery of the active agent, where localized delivery includes delivery where one or more medicaments contact the tooth and/or soft tissue areas, for example, the gingival margin of the mouth or a region of the inside of the mouth, or in close proximity thereto. The oral appliance may be used for localized and/or targeted delivery of the active agent to a patient to treat a disease or condition. Examples of diseases or conditions include, but, are not limited to, oral infections, inflamed and/or bleeding gums, mucosal wounds, lesions, ulcers, cold sores, tooth abscesses, gingivitis, periodontal disease, xerostomia, mouth malodor, hypertension, TMJ, migraines, GI ulcers, cardiac conditions, diabetes, neoplastic diseases, oral dermatologic diseases (e.g., lichen planus), hypothyroidism, hyperthyroidism, arthritis, or the like or combinations thereof.

Kits

In another aspect, a kit that comprises a device as described except that the active agent can be either included in the gap that exists between the polymer shells or can be provided in a form separate from the device with instructions for a user to insert the active agent in the gap prior to use. The device for including in the kit is generally of the form depicted, for example, in FIGS. 1A-1B and FIG. 2, where the first polymer shell and the second polymer shell can be joined along the respective edge members to form a gap, or can be joinable by a user to form a gap. The active agent is in a form for insertion into the gap, and can be inserted into the gap at the time of manufacture and provided in the kit with the active agent placed in the gap, or can be configured for a user to place the active agent into the gap. Upon placement of the device into the oral cavity, and more particularly onto or about the upper and/or lower teeth, the active agent is released from the gap and into the mouth cavity over a period of time.

From the foregoing, it can be appreciated that the device described herein provides a platform for delivery of essentially any agent. The gap or space between two adjacent polymer shells has a volume for carrying and delivering a desired dose of the agent. The selection of the material for manufacture of each polymer shell can vary, to design and control the rate of release of the agent. Agents that render the shell material porous to increase diffusion of the agent through the material can be included, or the shell material can be selected or treated to improve sorption of the agent into the material and diffusion through the material. Alternatively, control of the agent can be governed by the formulation inserted into the gap.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A device, comprising:

a first polymer shell contoured to fit at least a portion of a subject's upper or lower teeth, the first polymer shell having an inner surface, an outer surface, and a first shell edge member;

a second polymer shell dimensioned to receive the first polymer shell, the second polymer shell having an inner receiving surface and an outer external surface, and a second shell edge member, wherein the first edge member and the second edge member are joined to form a first gap between the outer surface and the inner receiving surface;

a first agent disposed in the first gap, wherein the device is configured for insertion into an oral cavity of a subject for delivery of the first agent for controlled release over a time period; and a third polymer shell dimensioned to receive the second polymer shell, the third polymer shell having an inner receiving surface and an outer external surface, and a third shell edge member; wherein the third shell edge member is comprised of an inner edge, an outer edge, or both an inner edge and an outer edge; and wherein the third shell edge member is joined at one or more discrete points to the second shell edge member, and where a second gap is formed between the inner receiving surface of the third shell member and the outer external surface of the second shell member.

2. The device of claim 1, wherein the first and second shell edge members are comprised of an inner edge, an outer edge, or both an inner edge and an outer edge; and wherein one or both of the inner edge and outer edge of the first and second shell edges form an arch.

3. The device of claim 2, wherein the inner edge and the outer edge of the second shell each form an arch with a length, respectively, of 12-inner and 12-outer, and the inner edge and the outer edge of the first shell each form an arch with a length, respectively, of 11-inner and 11-outer, and the first shell inner edge and the second shell inner edge are sealed along the lengths 11-inner and 12-inner, and the first shell outer edge and the second shell outer edge are sealed along the lengths 11-outer and 12-outer, to form a peripheral edge seal.

4. The device of claim 3, wherein the first agent is formulated with one or more excipients to obtain a formulation, and the controlled release of the first agent from the device is controlled by the peripheral edge seal.

5. A device comprising:

a first polymer shell contoured to fit at least a portion of a subject's upper or lower teeth, the first polymer shell having an inner surface, an outer surface, and a first shell edge member;

a second polymer shell dimensioned to receive the first polymer shell, the second polymer shell having an inner receiving surface and an outer external surface, and a second shell edge member, wherein the first edge member and the second edge member are joined to form a first gap between the outer surface and the inner receiving surface; and a first agent disposed in the first gap, wherein the device is configured for insertion into an oral cavity of a subject for delivery of the first agent for controlled release over a time period;

wherein the first and second shell edge members are comprised of an inner and an outer edge; and wherein the inner edge and the outer edge of the second shell each form an arch with a length, respectively, of 12-inner and 12-outer, and the inner edge and the outer edge of the first shell each form an arch with a length, respectively, of 11-inner and 11-outer, and the first shell inner edge and the second shell inner edge are sealed at one or more discrete points along the lengths 11-inner and 12-inner, and the first shell outer edge and the second shell outer edge are sealed at one or more discrete points along the lengths 11-outer and 12-outer, to form a plurality of peripheral edge sealing points.

6. The device of claim 5, wherein one or more of the first and second polymer shells has an opening.

7. The device of claim 5, wherein the device when inserted into an oral cavity of a subject is further configured to apply force to teeth for a wear period, for movement of teeth from an existing position to a next position.

8. The device of claim 5, wherein the device is a retainer, the retainer not configured to apply force to teeth to reach a final tooth position but to maintain teeth in a final tooth position, wherein the retainer is designed to be worn in the mouth for a wear period.

9. The device of claim 5, wherein the device is designed to be worn in the mouth, and wherein a wear period of the device is longer than the release period, or wherein the release period is longer than the wear period, or wherein the wear period and the release period are essentially the same.

10. The device of claim 5, where one or more of the first and second polymer shells is a laminate of at least two polymeric materials.

11. The device of claim 10, wherein the laminate is a di-laminate or a tri-laminate comprised a first thermoplastic material and a second thermoplastic material.

12. The device of claim 11, wherein the first thermoplastic material alone has a transparent appearance.

13. The device of claim 12, wherein the second thermoplastic material is translucent.

14. The device of claim 12, wherein the second thermoplastic material is a copolyester.

15. The device of claim 10, wherein the laminate comprises a transparent copolyester.

16. The device of claim 15, wherein the transparent copolyester is polyethylene terephthalate glycol-modified (PETG).

17. The device of claims 10, wherein the laminate comprises a polyurethane or a maleic anhydride grafted polyethylene.

18. The device of claim 17, wherein the laminate is a tri-laminate comprised of a middle layer of the polyurethane disposed between first and second layers of PETG.

19. The device of claim 17, wherein the laminate is a tri-laminate comprised of a middle layer of a PETG disposed between first and second layers of the polyurethane.

20. The device of claim 5, wherein the device comprises one or more agents.

21. The device of claim 20, further comprising a third polymer shell dimensioned to receive the second polymer shell, the third polymer shell having an inner receiving surface and an outer external surface, and a third shell edge member; wherein the third shell edge member is comprised of an inner edge, an outer edge, or both an inner edge and an outer edge; and wherein the third shell edge member is joined at one or more discrete points to the second shell edge member, where a second gap is formed between the inner receiving surface of the third shell member and the outer external surface of the second shell member; and wherein the one or more agents is a second agent and the second agent is disposed in the second gap.

22. The device of claim 21, wherein the second agent is configured to be released from the device at a rate different from the first agent.

23. The device of claim 5, wherein the first agent is formulated with one or more excipients to obtain a formulation, and the formulation controls the controlled release of the first agent from the device.

24. The device of claim 5, wherein the first agent is formulated with one or more excipients to obtain a formulation, and the controlled release of the first agent from the device is controlled by the first polymer shell or the second polymer shell.

25. The device of claim 5, wherein the first agent is formulated with one or more excipients to obtain a formulation, and the controlled release of the first agent from the device is controlled by the plurality of peripheral edge sealing points.

26. The device of claim 5, wherein one or more of the first and second polymer shells is a porous shell member.

27. The device of claim 5, wherein the first agent is a breath freshener, a nutritional agent or nutritional (dietary) supplement, an oral or dental wellness agent, or a therapeutic agent with activity for tissue remodeling.

28. The device of claim 27, wherein the first agent is selected from a group consisting of: vitamins, minerals, antioxidants, and sleep agents.

29. The device of claim 28, wherein the first agent is melatonin or 5-hydroxytryptophan.

30. The device of claim 27, wherein the first agent is stannous fluoride or sodium fluoride.

31. The device of claim 5, wherein the first agent is configured to be released over a period of at least about 6 hours, 8 hours, 12 hours, 18 hours, 24 hours, 36 hours, 48 hours or 72 hours.

32. The device of claim 5, wherein a support member is positioned in the first gap, wherein the support member is configured to releasably carry the first agent.

33. The device of claim 32, wherein the support member is foam, a population of microporous particles, or a fabric.

34. A kit, comprising:

a device, comprising:

a first polymer shell contoured to fit at least a portion of a subject's upper or lower teeth, the first polymer shell having an inner surface, an outer surface, and a first shell edge member;

a second polymer shell dimensioned to receive the first polymer shell, the second polymer shell having an inner receiving surface and an outer external surface, and a second shell edge member, wherein the first edge member and the second edge member are joined to form a gap between the outer surface and the inner receiving surface; and an agent configured for insertion into the gap;

wherein the device is configured for insertion into an oral cavity of a subject for delivery of the agent for controlled release over a time period;

wherein the first and second shell edge members are comprised of an inner and an outer edge; and wherein the inner edge and the outer edge of the second shell each form an arch with a length, respectively, of 12-inner and 12-outer, and the inner edge and the outer edge of the first shell each form an arch with a length, respectively, of 11-inner and 11-outer, and the first shell inner edge and the second shell inner edge are sealed at one or more discrete points along the lengths 11-inner and 12-inner, and the first shell outer edge and the second shell outer edge are sealed at one or more discrete points along the lengths 11-outer and 12-outer, to form a plurality of peripheral edge sealing points.

35. The kit of claim 34, further comprising one or more refills of the agent.

* * * * *